US 11,797,776 B2

(12) United States Patent
Khetan et al.

(10) Patent No.: US 11,797,776 B2
(45) Date of Patent: Oct. 24, 2023

(54) UTILIZING MACHINE LEARNING MODELS AND IN-DOMAIN AND OUT-OF-DOMAIN DATA DISTRIBUTION TO PREDICT A CAUSALITY RELATIONSHIP BETWEEN EVENTS EXPRESSED IN NATURAL LANGUAGE TEXT

(71) Applicant: Accenture Global Solutions Limited, Dublin (IE)

(72) Inventors: Vivek Kumar Khetan, San Francisco, CA (US); Mayuresh Anand, Santa Barbara, CA (US); Roshni Ramesh Ramnani, Karnataka (IN); Shubhashis Sengupta, Karnataka (IN); Andrew E. Fano, Lincolnshire, IL (US)

(73) Assignee: Accenture Global Solutions Limited, Dublin (IE)

( * ) Notice: Subject to any disclaimer, the term of this patent is extended or adjusted under 35 U.S.C. 154(b) by 257 days.

(21) Appl. No.: 17/248,298

(22) Filed: Jan. 19, 2021

(65) Prior Publication Data
US 2022/0075953 A1    Mar. 10, 2022

(30) Foreign Application Priority Data

Sep. 7, 2020    (IN) .............................. 202041038527

(51) Int. Cl.
*G06F 40/30*    (2020.01)
*G06F 40/284*    (2020.01)
(Continued)

(52) U.S. Cl.
CPC ............ *G06F 40/30* (2020.01); *G06F 40/284* (2020.01); *G06N 3/04* (2013.01); *G16H 70/40* (2018.01)

(58) Field of Classification Search
CPC ......... G06F 40/30; G06F 40/284; G06N 3/04; G06N 5/04; G06N 3/082; G06N 5/003;
(Continued)

(56) References Cited

U.S. PATENT DOCUMENTS

2016/0171383 A1* 6/2016 Narain ................... G16H 50/70
                                                               706/52
2019/0354850 A1* 11/2019 Watson ..................... G06N 3/08
(Continued)

OTHER PUBLICATIONS

Phang, Jason, et al. "Sentence encoders on stilts: Supplementary training on intermediate labeled-data tasks." arXiv preprint arXiv: 1811.01088 (2018), pp. 1-12 (Year: 2018).*
(Continued)

*Primary Examiner* — Jesse S Pullias
*Assistant Examiner* — Michael C. Lee
(74) *Attorney, Agent, or Firm* — Harrity & Harrity, LLP

(57) ABSTRACT

A device may receive training data that includes datasets associated with natural language processing, and may mask the training data to generate masked training data. The device may train a masked event C-BERT model, with the masked training data, to generate pretrained weights and a trained masked event C-BERT model, and may train an event aware C-BERT model, with the training data and the pretrained weights, to generate a trained event aware C-BERT model. The device may receive natural language text data identifying natural language events, and may process the natural language text data, with the trained masked event C-BERT model, to determine weights. The device may process the natural language text data and the weights, with the trained event aware C-BERT model, to predict causality relationships between the natural language events, and may perform actions, based on the causality relationships.

20 Claims, 10 Drawing Sheets

(51) Int. Cl.
 *G06N 3/04* (2023.01)
 *G16H 70/40* (2018.01)
(58) Field of Classification Search
 CPC ...... G06N 20/10; G06N 3/084; G06N 3/0454;
  G16H 70/40
 See application file for complete search history.

(56) References Cited

U.S. PATENT DOCUMENTS

2020/0372025 A1\* 11/2020 Yoon ..................... G06N 3/0454
2021/0151029 A1\*  5/2021 Gururani ................. A63F 13/53
2021/0326751 A1\* 10/2021 Liu ......................... G06N 3/084

OTHER PUBLICATIONS

Dasgupta, Tirthankar, et al. "Automatic extraction of causal relations from text using linguistically informed deep neural networks." Proceedings of the 19th Annual SIGdial Meeting on Discourse and Dialogue. 2018, pp. 306-316 (Year: 2018).\*

Lee, Jinhyuk, et al. "BioBERT: a pre-trained biomedical language representation model for biomedical text mining." Bioinformatics, (published Sep. 10, 2019), pp. 1234-1240 (Year: 2019).\*

Liu, Yinhan, et al. "Roberta: A robustly optimized bert pretraining approach." arXiv preprint arXiv:1907.11692 (2019) (Year: 2019).\*

Yu, Bei, et al. "Detecting causal language use in science findings." EMNLP-IJCNLP (2019) pp. 4664-4674. (Year: 2019).\*

Ding, Xiao, et al. "ELG: an event logic graph." arXiv preprint arXiv:1907.08015 (2019), pp. 1-11 (Year: 2019).\*

"NVIDIA DGX-1: The Essential Instrument for All Research" (Jul. 2019) datasheet (Year: 2019).\*

Pruksachatkun, Yada, et al. "Intermediate-task transfer learning with pretrained models for natural language understanding: When and why does it work?." arXiv preprint arXiv:2005.00628 (May 9, 2020) (Year: 2020).\*

Kayesh, Humayun, et al. "Answering binary causal questions: A transfer learning based approach." 2020 International Joint Conference on Neural Networks (IJCNN). IEEE, (Jul. 2020). (Year: 2020).\*

Bouraoui, Zied, et a. "Inducing relational knowledge from BERT." Proceedings of the AAAI Conference on Artificial Intelligence. (Apr. 3, 2020), pp. 7456-7463 (Year: 2020).\*

Veitch, Victor, et al. "Adapting Text Embeddings for Causal Inference." arXiv preprint arXiv:1905.12741 v.2 (Jul. 25, 2020) pp. 1-10 (Year: 2020).\*

Beamer et al. "UIUC: A Knowledge-rich Approach to Identifying Semantic Relations between Nominals," Proceedings of the 4th International Workshop on Semantic Evaluations, Jun. 2007, pp. 386-389.

Church et al., "Word Association Norms, Mutual Information, and Lexicography," Computational Linguistics vol. 16, No. 1, Mar. 1990, pp. 22-29.

Dasgupta et al., "Automatic Extraction of Causal Relations from Text using Linguistically Informed Deep Neural Networks," Proceedings of the SIGDIAL 2018 Conference, Jul. 12-14, 2018, pp. 306-316.

Devlin et al., "BERT: Pre-training of Deep Bidirectional Transformers for Language Understanding," Proceedings of NAACL-HLT, Jun. 2-7, 2019, pp. 4171-4186.

Do et al., "Minimally Supervised Event Causality Identification," Proceedings of the 2011 Conference on Empirical Methods in Natural Language Processing, Jul. 27-31, 2011, pp. 294-303.

Dunietz et al.," The BECauSE Corpus 2.0: Annotating Causality and Overlapping Relations," Proceedings of the 11th Linguistic Annotation Workshop, Apr. 3, 2017, pp. 95-104.

Daniela Garcia, "COATIS, an NPL System to Locate Expressions of Actions Connected by Causality Links," Lecture Notes in Computer Science (including subseries Lecture Notes in Artificial Intelligence and Lecture Notes in Bioinformatics), 1319 (Section 2), 1997, pp. 347-352.

Roxana Girju, "Automatic Detection of Causal Relations for Question Answering," Proceedings of the ACL 2003 workshop on Multilingual summarization and question answering, 2003, pp. 76-83.

Girju et al., "Text Mining for Causal Relations," Proceedings of the FLAIRS Conference, 2002, pp. 360-364.

Girju et al., "SemEval-2007 Task 04: Classification of Semantic Relations between Nominals," Proceedings of the 4th International Workshop on Semantic Evaluations, Jun. 2007, pp. 13-18.

Yoav Goldberg, "Assessing BERT's Syntactic Abilities," arXiv: 1901.05287v1 [cs.CL], Jan. 16, 2019, 4 Pages.

Gordon et al., "Commonsense Causal Reasoning Using Millions of Personal Stories," Proceedings of the National Conference on Artificial Intelligence, 2011, pp. 1180-1185.

Gurulingappa et al., "Development of a benchmark corpus to support the automatic extraction of drug-related adverse effects from medical case reports," Journal of Biomedical Informatics, vol. 45, No. 5, 2012, pp. 885-892.

Gururangan et al., "Don't Stop Pretraining: Adapt Language Models to Domains and Tasks," arXiv: 2004.10964v3 [cs.CL], May 5, 2020, 19 Pages.

Hassanzadeh et al., "Answering Binary Causal Questions Through Large-Scale Text Mining: An Evaluation Using Cause-Effect Pairs from Human Experts," Proceedings of the Twenty-Eighth International Joint Conference on Artificial Intelligence, Aug. 2019, pp. 5003-5009.

Hassanzadeh et al., "Causal Knowledge Extraction through Large-Scale Text Mining," The Thirty-Fourth AAAI Conference on Artificial Intelligence, 2020, pp. 13610-13611.

Hendrickx et al., "SemEval-2010 Task 8: Multi-Way Classification of Semantic Relations Between Pairs of Nominals," Proceedings of the 5th International Workshop on Semantic Evaluation, Jul. 15-16, 2010, pp. 33-38.

Hu et al., "Inference of Fine-Grained Event Causality from Blogs and Films," arXiv:1708.09453v1 [cs.CL], Aug. 30, 2017, 7 Pages.

Huynh et al., "Adverse Drug Reaction Classification With Deep Neural Networks," Proceedings of COLING 2016, the 26th International Conference on Computational Linguistics: Technical Papers, Dec. 11-16, 2016, pp. 877-887.

Jawahar et al., "What does BERT learn about the structure of language?," Proceedings of the 57th Annual Meeting of the Association for Computational Linguistics, Jul. 28-Aug. 2, 2019, pp. 3651-3657.

Khoo et al., "Extracting Causal Knowledge from a Medical Database Using Graphical Patterns," Proceedings of the 38th annual meeting of the association for computational linguistics, 2000, pp. 336-343.

Luo et al., "Commonsense Causal Reasoning between Short Texts," Proceedings, Fifteenth International Conference on Principles of Knowledge Representation and Reasoning, 2016, pp. 421-430.

Mihalcea et al., "Corpus-based and Knowledge-based Measures of Text Semantic Similarity," Proceedings of the National Conference on Artificial Intelligence, 2006, pp. 775-780.

Mirza et al., "Annotating causality in the TempEval-3 corpus," Proceedings of the EACL 2014 Workshop on Computational Approaches to Causality in Language, Apr. 26, 2014, pp. 10-19.

Judea Pearl, "Causal inference in statistics: An overview," Statistics Surveys, vol. 3, 2009, pp. 96-146.

Prasad et al., "The Penn Discourse TreeBank 2.O.," LREC. Citeseer, 2008, pp. 2961-2968.

James Pustejovsky, "The Syntax of Event Structure," Cognition, vol. 41, 1991, pp. 33-60.

Sharp et al., "Creating Causal Embeddings for Question Answering with Minimal Supervision," Proceedings of the 2016 Conference on Empirical Methods in Natural Language Processing, Nov. 1-5, 2016, pp. 138-148.

Soares et al., "Matching the Blanks: Distributional Similarity for Relation Learning," Proceedings of the 57th Annual Meeting of the Association for Computational Linguistics, Jul. 28-Aug. 2, 2019, pp. 2895-2905.

(56) References Cited

OTHER PUBLICATIONS

Vaswani et al., "Attention Is All You Need," 31st Conference on Neural Information Processing Systems, 2017, pp. 1-11.
Wu et al., "Enriching Pre-trained Language Model with Entity Information for Relation Classification," International Conference on Information and Knowledge Management, Proceedings, May 20, 2019, 6 Pages.

* cited by examiner

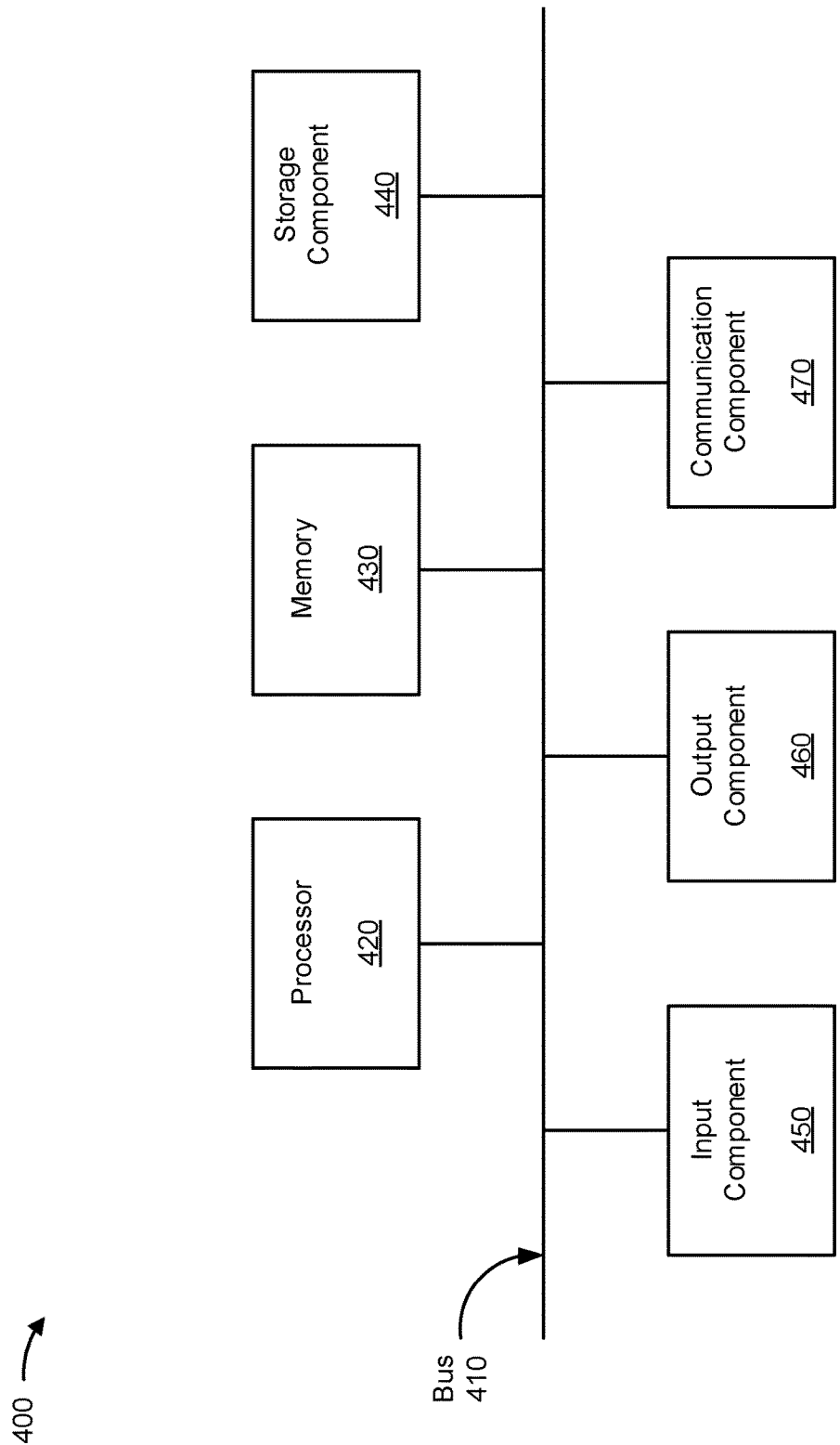

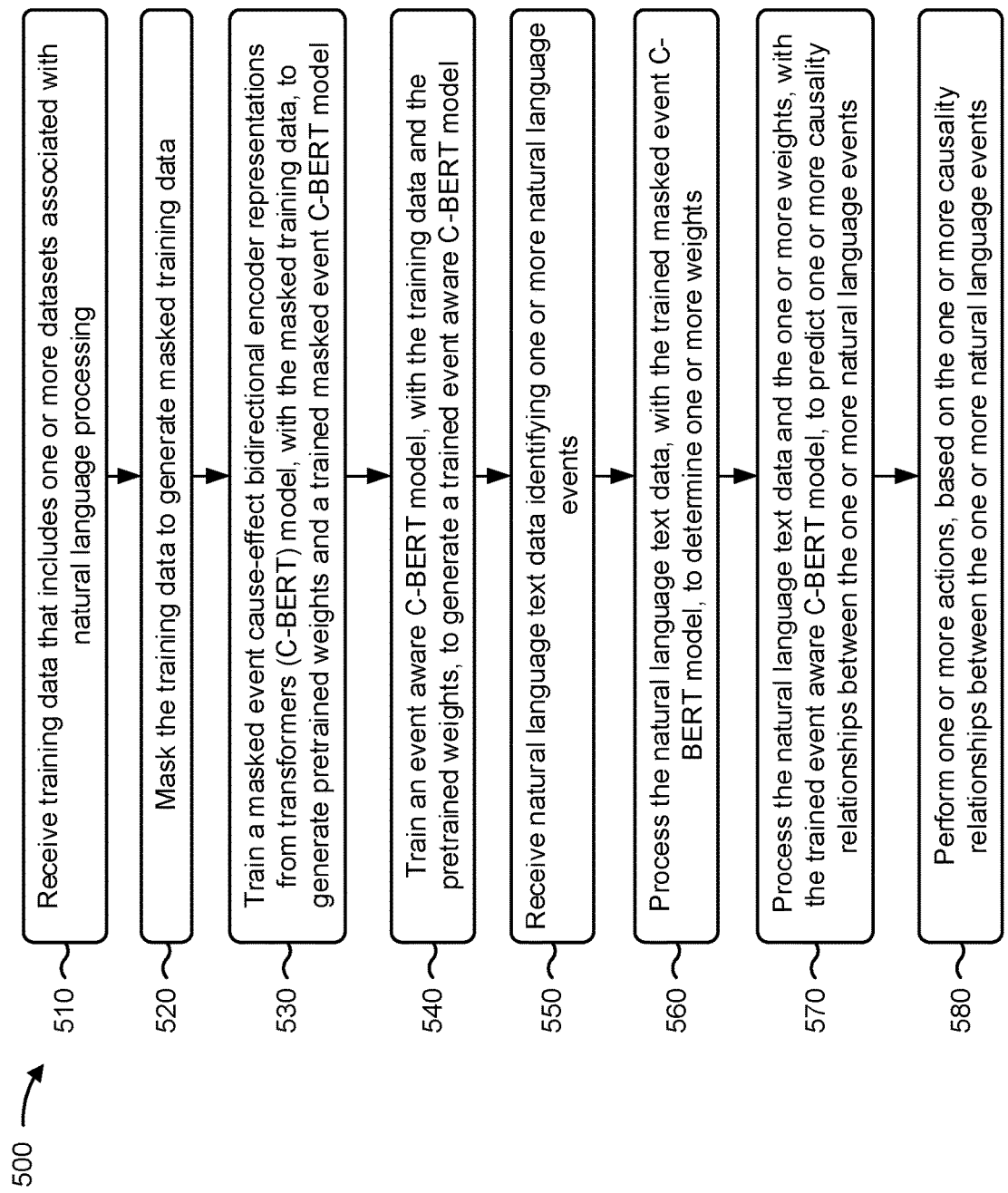

UTILIZING MACHINE LEARNING MODELS AND IN-DOMAIN AND OUT-OF-DOMAIN DATA DISTRIBUTION TO PREDICT A CAUSALITY RELATIONSHIP BETWEEN EVENTS EXPRESSED IN NATURAL LANGUAGE TEXT

CROSS-REFERENCE TO RELATED APPLICATION

This patent application claims priority to India Provisional Patent Application No. 202041038527, filed on Sep. 7, 2020, and entitled "UTILIZING MACHINE LEARNING MODELS AND IN-DOMAIN AND OUT-OF-DOMAIN DATA DISTRIBUTION TO PREDICT A CAUSE-EFFECT RELATIONSHIP BETWEEN EVENTS EXPRESSED IN NATURAL LANGUAGE TEXT." The disclosure of the prior application is considered part of and is incorporated by reference into this patent application.

BACKGROUND

The current euphoria in artificial intelligence advancement is often questioned due to contemporary methods' limited understanding of causality among events. Efforts around causality can be grouped into causal discovery and causality understanding for events described in natural language text. Causality detection in natural language is often described as detection of cause-effect between two events, where events are expressed as nominal, phrases, or short span of text in the same or different sentences.

SUMMARY

In some implementations, a method includes receiving training data that includes one or more datasets associated with natural language processing, and masking the training data to generate masked training data. The method may include training a masked event cause-effect bidirectional encoder representations from transformers (C-BERT) model, with the masked training data, to generate pretrained weights and a trained masked event C-BERT model, and training an event aware C-BERT model, with the training data and the pretrained weights, to generate a trained event aware C-BERT model. The method may include receiving natural language text data identifying one or more natural language events, and processing the natural language text data, with the trained masked event C-BERT model, to determine one or more weights. The method may include processing the natural language text data and the one or more weights, with the trained event aware C-BERT model, to predict one or more causality relationships between the one or more natural language events, and performing one or more actions, based on the one or more causality relationships between the one or more natural language events.

In some implementations, a device may include one or more memories and one or more processors to receive training data that includes one or more datasets associated with natural language processing, and replace event descriptions, provided in the training data, with blank tokens to generate masked training data. The one or more processors may train a masked event C-BERT model, with the masked training data, to generate pretrained weights and a trained masked event C-BERT model, and may train an event aware C-BERT model, with the training data and the pretrained weights, to generate a trained event aware C-BERT model. The one or more processors may receive natural language text data identifying one or more natural language events, and may process the natural language text data, with the trained masked event C-BERT model, to determine one or more weights. The one or more processors may process the natural language text data and the one or more weights, with the trained event aware C-BERT model, to predict one or more causality relationships between the one or more natural language events, and may perform one or more actions, based on the one or more causality relationships between the one or more natural language events.

In some implementations, a non-transitory computer-readable medium may store a set of instructions that includes one or more instructions that, when executed by one or more processors of a device, cause the device to receive data that includes one or more datasets associated with natural language processing, and annotate one or more sentences, provided in the one or more datasets, with event descriptions to generate annotated data. The one or more instructions may cause the device to assign one or more labels for each pair of event interactions, provided in the one or more datasets, to generate labeled data, and combine the annotated data and the labeled data to form training data. The one or more instructions may cause the device to mask the training data to generate masked training data, and train a masked event C-BERT model, with the masked training data, to generate pretrained weights and a trained masked event C-BERT model. The one or more instructions may cause the device to train an event aware C-BERT model, with the training data and the pretrained weights, to generate a trained event aware C-BERT model, and receive natural language text data identifying one or more natural language events. The one or more instructions may cause the device to process the natural language text data, with the trained masked event C-BERT model, to determine one or more weights, and process the natural language text data and the one or more weights, with the trained event aware C-BERT model, to predict one or more causality relationships between the one or more natural language events. The one or more instructions may cause the device to perform one or more actions, based on the one or more causality relationships between the one or more natural language events.

BRIEF DESCRIPTION OF THE DRAWINGS

FIG. 4 is a diagram of example components of one or more devices of FIG. 3.

FIG. 5 is a flowchart of an example process for utilizing machine learning models and in-domain and out-of-domain data distribution to predict a causality relationship between events expressed in natural language text.

DETAILED DESCRIPTION

Figure 1A:
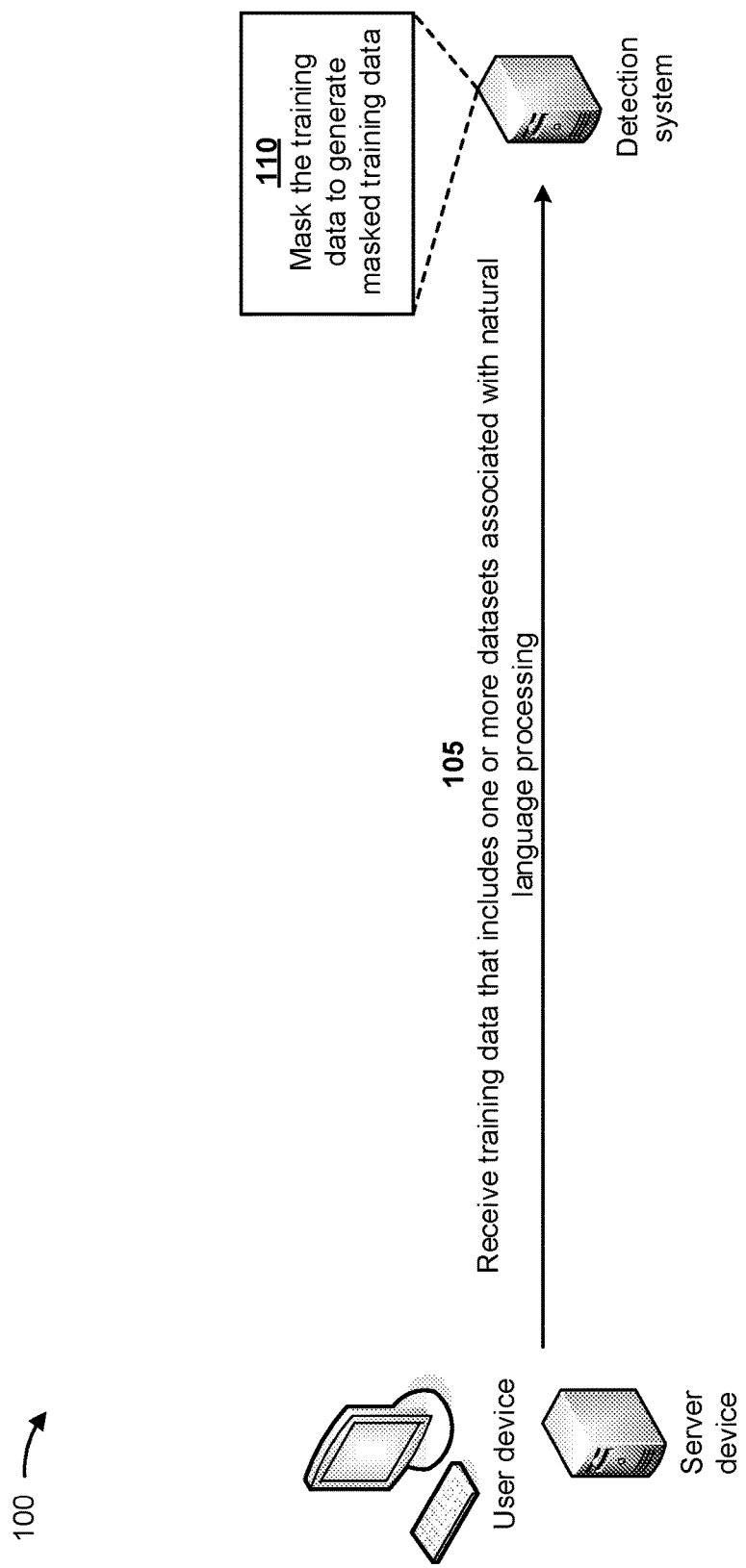
FIGS. 1A-1F are diagrams of an example implementation described herein.

The following detailed description of example implementations refers to the accompanying drawings. The same reference numbers in different drawings may identify the same or similar elements.

Causality detection is necessary for language understanding, and may be used in various domains, such as linguistics, economics, and medicine. Understanding a potential cause-effect relationship between events may help in binary causal question answering, plausible understating of the relationship between everyday activities, adverse drug effect, drug-drug interaction mentioned in medical text, and various decision support tasks.

Most current methods for causality understanding write linguistic pattern-matching rules or use careful feature engineering to train a supervised machine learning model. However, current methods lack coverage and are difficult to scale for any unseen sequence of text, as event interaction depends on an entire sentence structure, along with semantic features of the sentence. Additionally, current methods are unable to decompose every event and remaining portions of an expression completely in a lexical representation. Furthermore, a lack of publicly available annotated datasets for cause-effect has limited proposals of deep learning-based approaches. Thus, current methods for causality understanding waste human resources, computing resources (e.g., processing resources, memory resources, communication resources, and/or the like), networking resources, and/or the like associated with manually training supervised machine learning models, generating machine learning models that are incomplete, generating machine learning models that do not scale, and/or the like.

Some implementations described herein relate to a detection system that utilizes machine learning models and in-domain and out-of-domain data distribution to predict a causality relationship (also referred to as a cause-effect relationship) between events expressed in natural language text. For example, the detection system may receive training data that includes one or more datasets associated with natural language processing, and may mask the training data to generate masked training data. The detection system may train a masked event C-BERT model, with the masked training data, to generate pretrained weights and a trained masked event C-BERT model, and may train an event aware C-BERT model, with the training data and the pretrained weights, to generate a trained event aware C-BERT model. The detection system may receive natural language text data identifying one or more natural language events, and may process the natural language text data, with the trained masked event C-BERT model, to determine one or more weights. The detection system may process the natural language text data and the one or more weights, with the trained event aware C-BERT model, to predict one or more causality relationships between the one or more natural language events, and may perform one or more actions, based on the one or more causality relationships between the one or more natural language events.

In this way, the detection system utilizes machine learning models and in-domain and out-of-domain data distribution to predict a causality relationship between events expressed in natural language text. The detection system may provide an understanding of causality between events expressed in the natural language text. The events may be a nominal, a phrase, or a span of text in an event statement. The detection system may utilize language models and variants of language models that combine event information, sentence argument structure, and overall sentence context to determine the causality understanding between events. For example, the language models may determine a cause-effect interaction between events expressed in a text expression. Pre-training the language models with out-of-domain data distribution improves performance of the language models, and indicates that the language models may learn implicit structural representation in natural language text. This, in turn, conserves human resources, computing resources, networking resources, and/or the like that would otherwise have been wasted by manually training supervised machine learning models, generating machine learning models that are incomplete, generating machine learning models that do not scale, and/or the like.

FIGS. 1A-1F are diagrams of an example 100 associated with utilizing machine learning models and in-domain and out-of-domain data distribution to predict a causality relationship between events expressed in natural language text. As shown in FIGS. 1A-1F, example 100 includes a user device and a server device associated with a detection system. The user device may include a laptop computer, a mobile telephone, a desktop computer, and/or the like utilized by a user (e.g., a security analyst). The server device may include a device that collects and/or determines contextual data, computational data, experiential data, and industry data associated with software code. The detection system may include a system that utilizes machine learning models and in-domain and out-of-domain data distribution to predict a causality relationship between events expressed in natural language text.

As shown in FIG. 1A, and by reference number 105, the detection system may receive training data that includes one or more datasets associated with natural language processing. In some implementations, the one or more datasets include a Semeval 2007 dataset, a Semeval 2010 dataset, an adverse drug effect (ADE) dataset, a drug-drug interaction (DDI) dataset, and/or the like.

The Semeval 2007 dataset is an evaluation task dataset designed to provide a framework for comparing different approaches to classifying semantic relations between nominals in a sentence. The Semeval 2007 dataset provides datasets for different semantic relations, including "cause-effect" relations. For a given sentence, if an interaction between a marked event is causal, the sentence may be labeled as "cause-effect." Otherwise, the sentence may be labeled as "other." The Semeval 2010 dataset is similar to the Semeval 2007 dataset. The Semeval 2010 dataset may include causal interactions between events that are labeled as "cause-effect," and other types of interactions between the events that are labeled as "other."

The ADE dataset is a collection of biomedical text annotated with drugs and the adverse effects of the drugs. The ADE dataset may include data identifying drugs causing adverse effects, annotations for the adverse effects, data identifying drugs not causing side effects, annotations for the drugs not causing side effects, and/or the like. The DDI dataset includes a knowledge base describing clinical level information about drugs, such as side effects and drug interactions, as well as molecular level data such as chemical structures and with which proteins a drug interacts.

The one or more datasets may include one or more sentences and one or more pairs of event interactions. In some implementations, the detection system may annotate the one or more sentences with event descriptions, and may assign one or more labels for each pair of the one or more pairs of event interactions. In such implementations, the one or more datasets, the annotated sentences, and the labeled pairs of event interactions may form the training data.

As further shown in FIG. 1A, and by reference number 110, the detection system may mask the training data to generate masked training data. For example, the detection system may replace event descriptions, provided in the training data, with blank tokens to generate the masked training data. In some implementations, the detection system adds event markers to events in sentences of the one or more datasets and adds masked event markers to the events in the sentences of the one or more datasets (e.g., to generate the masked training data). For example, the detection system may add event markers and masked event markers as shown in the following table.

| Dataset | Example Sentence | Sentence with event markers | Sentence with masked event markers |
| --- | --- | --- | --- |
| Semeval 2007 | Most of the taste of strong onions comes from the smell. | Most of the <e1> taste </e1> of strong onions comes from the <e2> smell</e2>. | Most of the <e1> blank </e1> of strong onions comes from the <e2> blank </e2>. |
| Semeval 2010 | As in the popular movie "Deep Impact," the action of the Perseid meteor shower is caused by a comet, in this case periodic comet Swift-Tuttle. | As in the popular movie "Deep Impact," the action of the Perseid <e1> meteor shower </e1> is caused by a <e2> comet </e2>, in this case periodic comet Swift-Tuttle. | As in the popular movie "Deep Impact," the action of the Perseid <e1> blank </e1> is caused by a <e2> blank </e2>, in this case periodic comet Swift-Tuttle. |
| ADE | Quinine induced coagulopathy-a near fatal experience. | <e2> Quinine </e2> induced <e1> coagulopathy </e1>-a near fatal experience. | <e2> blank </e2> induced <e1> blank </e1>-a near fatal experience. |

Figure 1B:
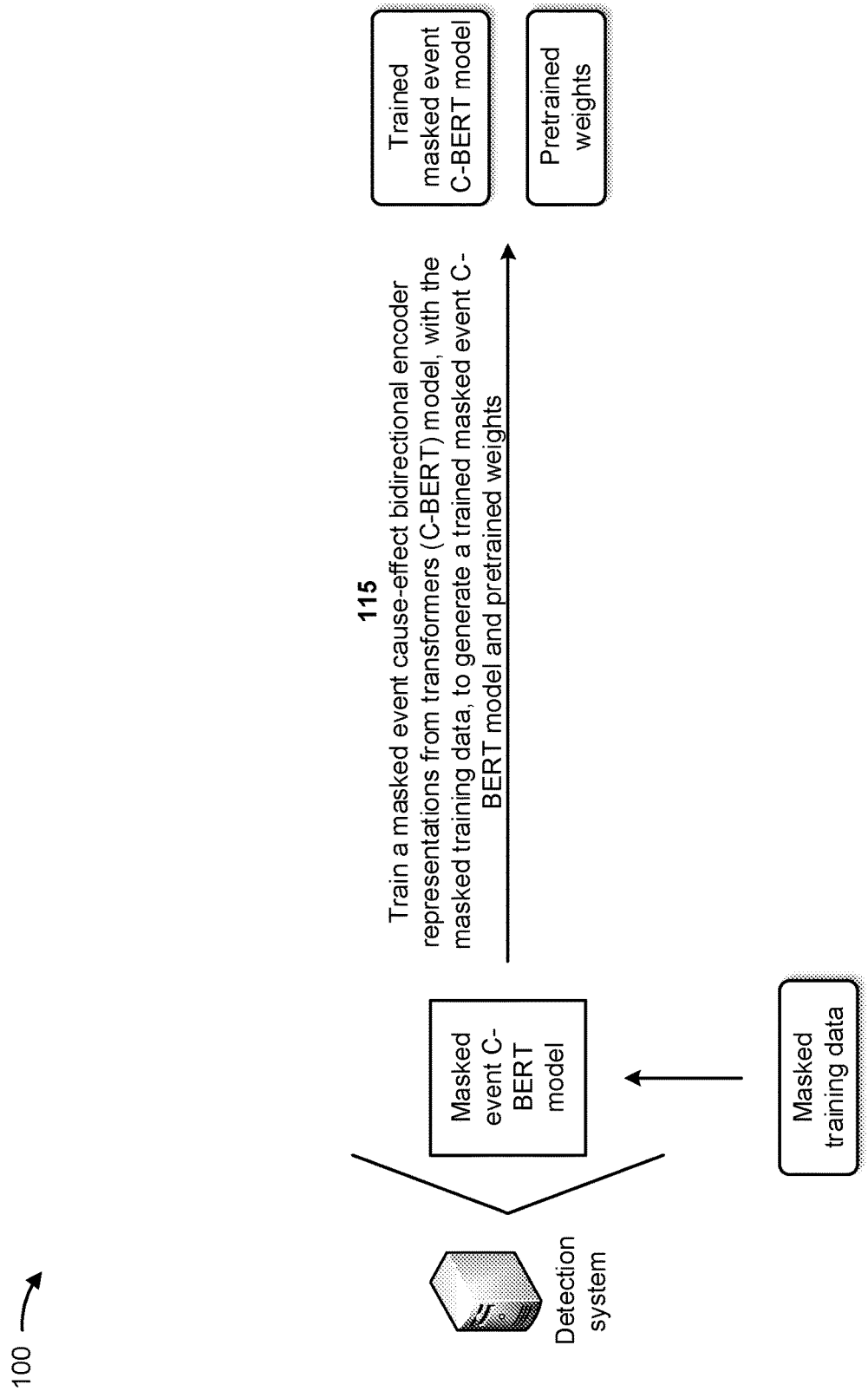

As shown in FIG. 1B, and by reference number 115, the detection system may train a masked event C-BERT model, with the masked training data, to generate a trained masked event C-BERT model and pretrained weights. The pretrained weights may include weights to apply to the training data when the training data is utilized to train an event aware C-BERT model, as described below in connection with FIG. 1C. A bidirectional encoder representations from transformers (BERT) model is a pre-trained language model based on a transformer architecture. A BERT model provides deep bidirectional representations from unlabeled text by jointly conditioning on left and right contexts. BERT-based pretrained models may be utilized with several tasks, such as question-answer tasks, relation extraction tasks, natural language inference (NLI) tasks, and/or the like.

The C-BERT model may include a feed-forward neural network model that is built on a pretrained BERT model. The C-BERT model may be trained for binary classification of a "cause-effect" or "other" relationship between two events in a given input sentence. The C-BERT model may receive the input sentence as a sequence of tokens and may output an overall sentence context vector based on the input sentence. The C-BERT model may provide the sentence context vector to a non-linear activation layer followed by two fully connected layers. A dropout with a probability of 0.4 may be applied before each fully connected layer. A softmax layer of the C-BERT model may provide a likelihood of an interaction being a "cause-effect" interaction. The C-BERT model may utilize back-propagation with an Adam optimizer on a binary loss function to learn an optimal solution. A mathematical formulation for the C-BERT model may include the following:

$H_0' = W_0(\tanh(H_0)) + b_0$ $h'' = W_1(H_0') + b_1$ $p = \text{softmax}(h'')$, where $W_0 \in R^{d \times d}$ (a context vector); $W_1 \in R^{L \times d}$ (a context vector); $H_0$ is an output token of a bi-directional context of BERT; and L=2 (cause-effect, other).

The masked event C-BERT model may include a feed-forward neural network model that is built on a pretrained BERT model. The masked event C-BERT model is similar to the event aware C-BERT model, described below in connection with FIG. 1C, but may include event text that is replaced with a blank token. Since each event is a single blank token, the masked event C-BERT model may determine a final context of any event without determining an average. In some implementations, the detection system fine-tunes the masked event C-BERT model with actual event information and utilizing the event aware C-BERT model described below. A mathematical formulation for the masked event C-BERT model may include the following:

$H_0' = W_0(\tanh(H_0)) + b_0$ $H_1' = W_1(\tanh(H_{ij})) + b_1$ $H_2' = W_2(\tanh(H_{km})) + b_2$ $h'' = W_3(\text{concat}(H_0', H_1', H_2')) + b_3$ $p = \text{softmax}(h'')$, where $W_0$, $W_1$, $W_2 \in R^{d \times d}$ (a context vector); $W_3 \in R^{L \times 3d}$ (a context vector); $H_0$ is an output token of a bi-directional context of BERT; and L=2 (cause-effect, other).

Figure 1C:
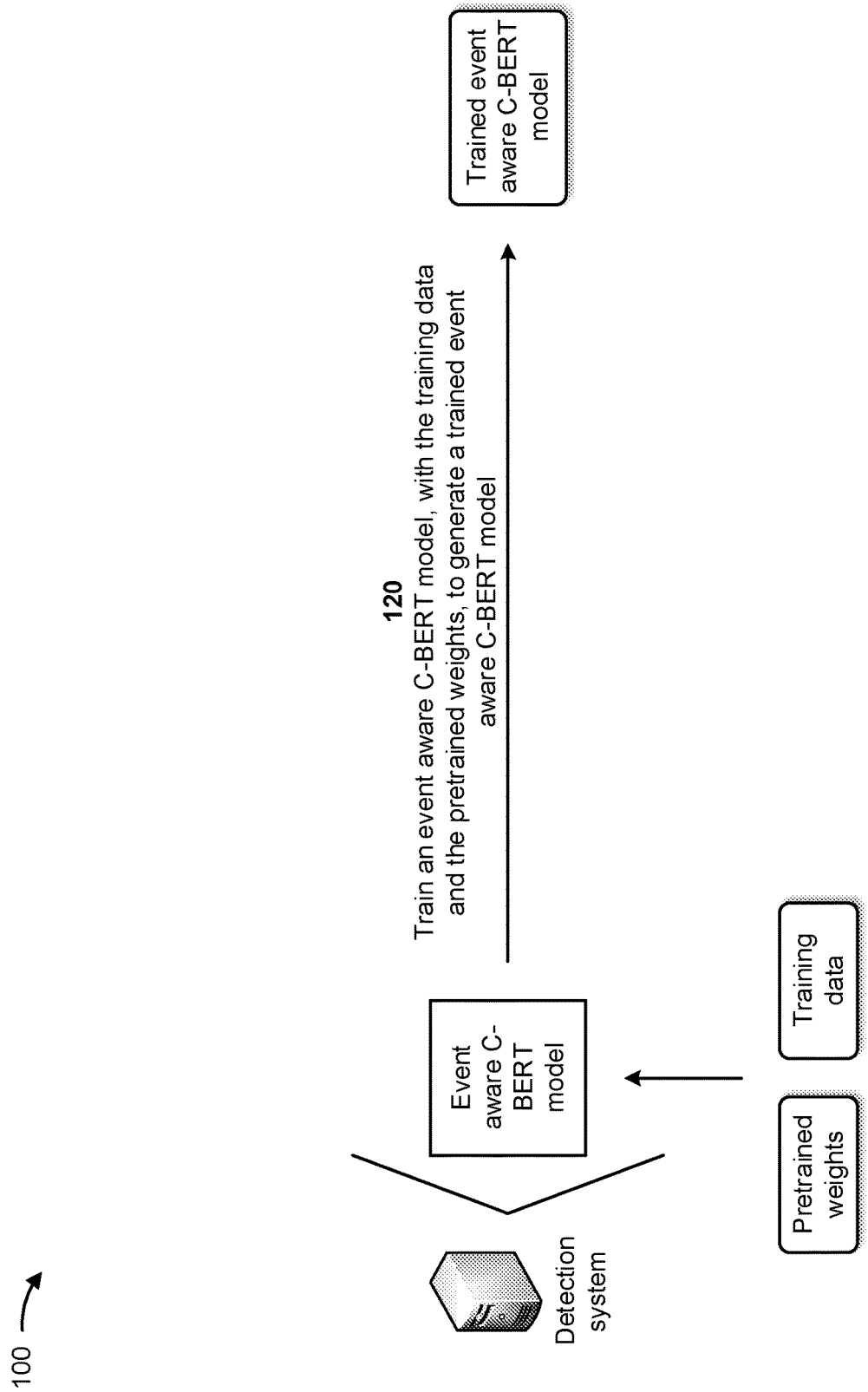

As shown in FIG. 1C, and by reference number 120, the detection system may train an event aware C-BERT model, with the training data and the pretrained weights, to generate a trained event aware C-BERT model. For example, the detection system may apply the pretrained weights to the training data to generate weighted training data, and may train the event aware C-BERT model with the weighted training data to generate the trained event aware C-BERT model.

The event aware C-BERT model may include a feed-forward neural network model that is built on a pretrained BERT model. The event aware C-BERT model may learn an event-informed representation of a sentence and may predict one or more causality relationships between identified (e.g., marked) events of the sentence. Events of the sentence may include more than a single token, which may result in many vectors being generated for the sentence and input into a pretrained BERT model. The event aware C-BERT model may average the vectors to determine a final context of each event expression. The event aware C-BERT model may provide the final contexts and the sentence context to a non-linear activation layer followed by a fully connected layer. The sentence context may be concatenated with an averaged context of the events and provided to another fully connected layer followed by a softmax layer. A dropout with a probability of 0.4 may be applied before each fully connected layer. The softmax layer of the event aware C-BERT model may provide a likelihood of an interaction being a "cause-effect" interaction. The event aware C-BERT model may utilize back-propagation with an Adam optimizer on a binary loss function to predict a "cause-effect" or "other" relationship between events. A mathematical formulation for the event aware C-BERT model may include the following:

$$H'_0 = W_0(\tanh(H_0)) + b_0$$

$$H'_1 = W_1 \left[ \frac{1}{j-i+1} \sum_{t=i}^{j} \tanh(H_t) \right] + b_1$$

$$H'_2 = W_2 \left[ \frac{1}{j-i+1} \sum_{t=i}^{j} \tanh(H_t) \right] + b_2$$

$$h'' = W_3(concat(H'_0, H'_1, H'_2)) + b_3$$

$$p = \text{softmax}(h'')$$

where $W_0$, $W_1$, $W_2 \in R^{d \times d}$ (a context vector); $W_3 \in R^{L \times 3d}$ (a context vector); $H_0$ is an output token of a bi-directional context of BERT; and L=2 (cause-effect, other).

In some implementations, the training data utilized to train the masked event C-BERT model and the event aware C-BERT model includes in-domain and out-of-domain text expressions. The in-domain and out-of-domain text expressions may enable the masked event C-BERT model and the event aware C-BERT model to implicitly learn sentence structure for event causality. The detection system may fine-tune the event aware C-BERT model to determine and assign cause-effect and other relationship labels between events expressed in natural language text. The detection system may combine the events' context with an overall sentence representation (e.g., determined by the event aware C-BERT model) to predict the cause-effect and other relationship labels between the events. The detection system may also combine the events' masked context with the overall sentence representation (e.g., determined by the masked event C-BERT model) to implicitly learn a sentence argument structure using the in-domain and out-of-domain text expressions.

Figure 1D:
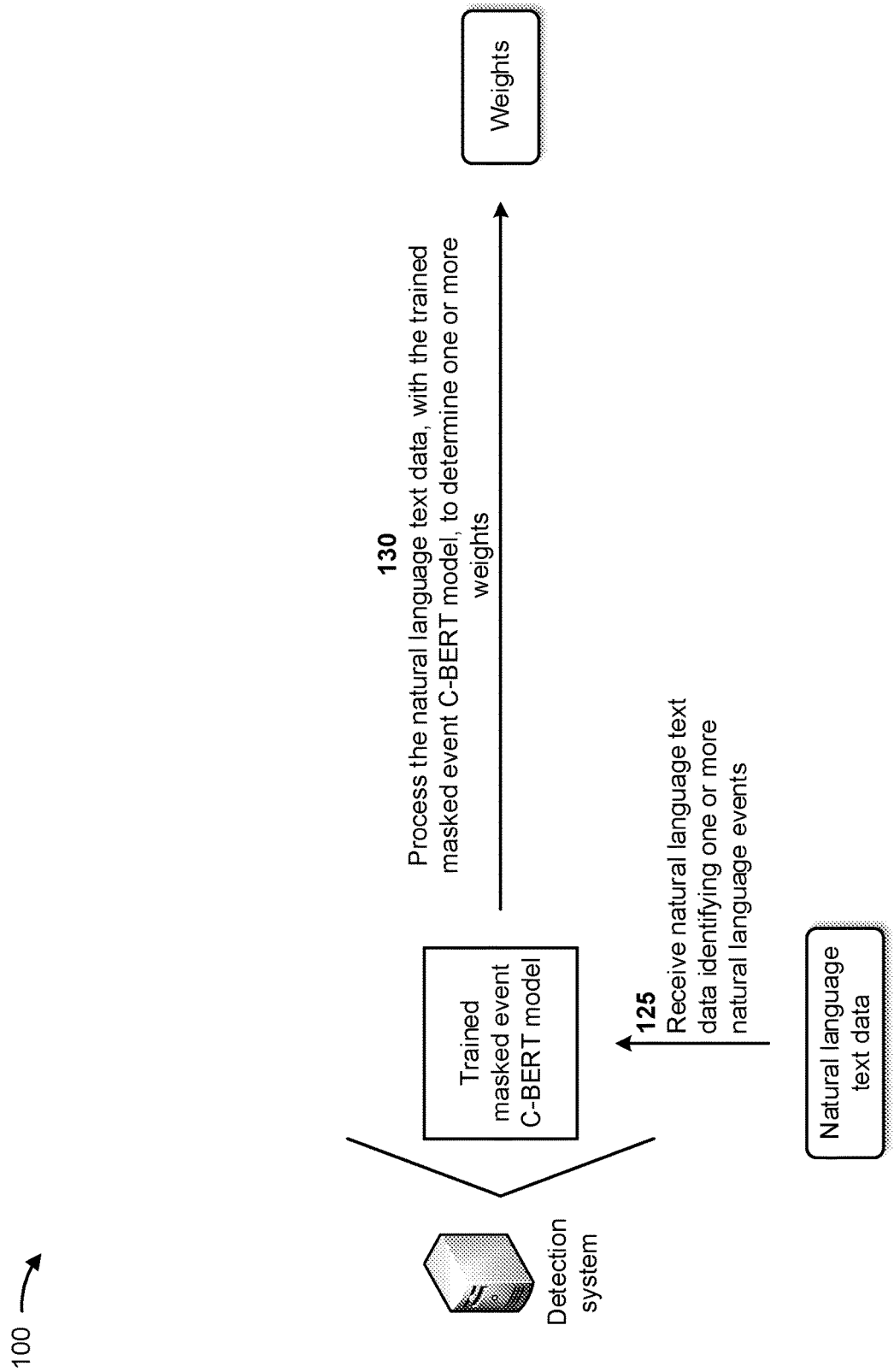

As shown in FIG. 1D, and by reference number 125, the detection system may receive natural language text data identifying one or more natural language events. For example, the detection system may receive the natural language text data from the user device and/or the server device. The natural language text data may include sentences and each of the one or more natural language events may include a nominal in a same sentence or different sentences, a phrase in a same sentence or different sentences, a span of text in a same sentence or difference sentences, and/or the like.

As further shown in FIG. 1D, and by reference number 130, the detection system may process the natural language text data, with the trained masked event C-BERT model, to determine one or more weights. The one or more weights may include weights to apply to the natural language text data when the natural language text data is processed by the trained event aware C-BERT model, as described below in connection with FIG. 1E.

Figure 1E:
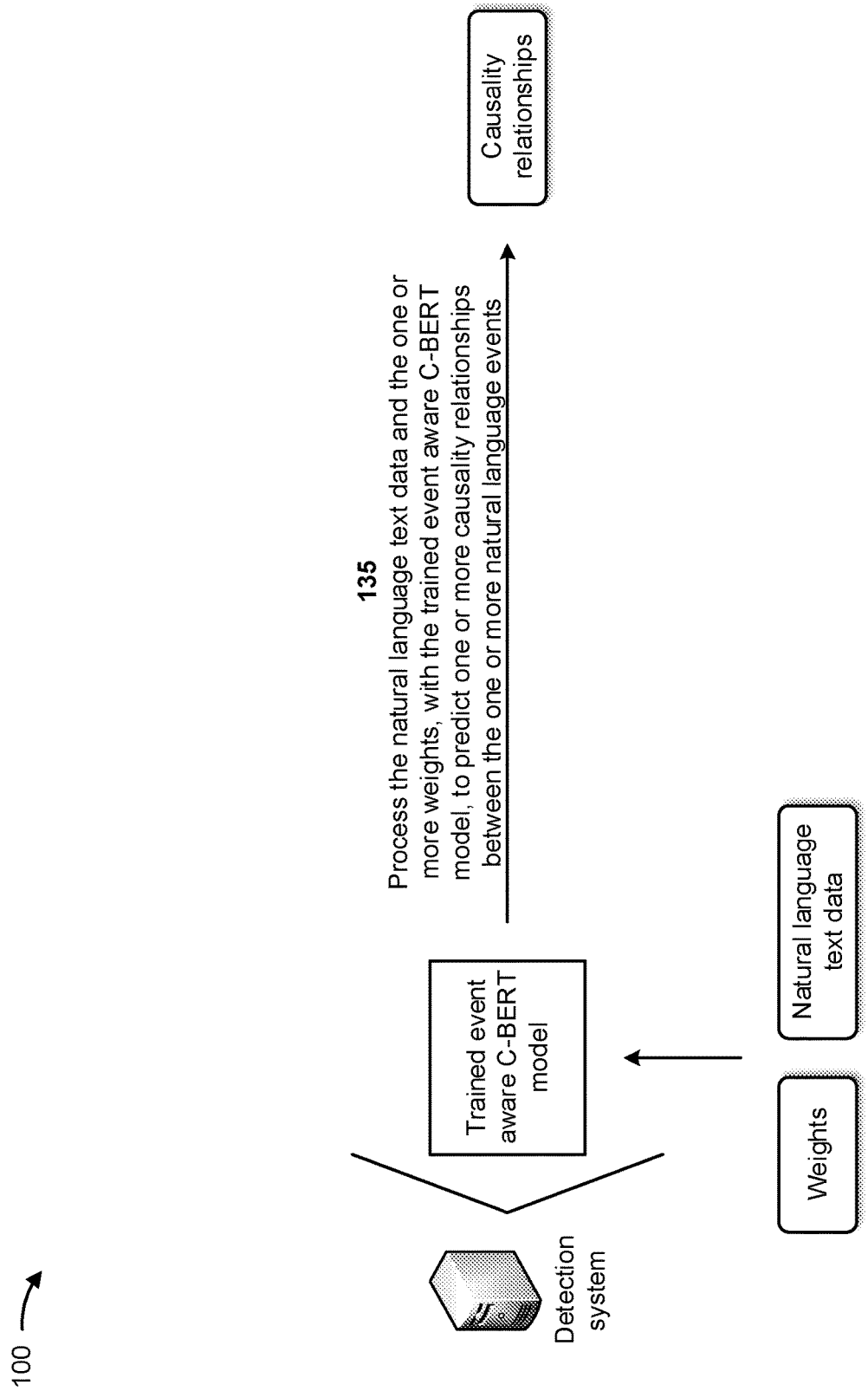

As shown in FIG. 1E, and by reference number 135, the detection system may process the natural language text data and the one or more weights, with the trained event aware C-BERT model, to predict one or more causality relationships between the one or more natural language events. For example, the detection system may apply the one or more weights to the natural language text data to generate weighted natural language text data, and may process the weighted natural language text data, with the trained event aware C-BERT model, to predict the one or more causality relationships between the one or more natural language events. The one or more causality relationships may include relationships between two of the natural language events expressed as nominals, phrases, or short spans of text in the same or difference sentences.

Figure 1F:
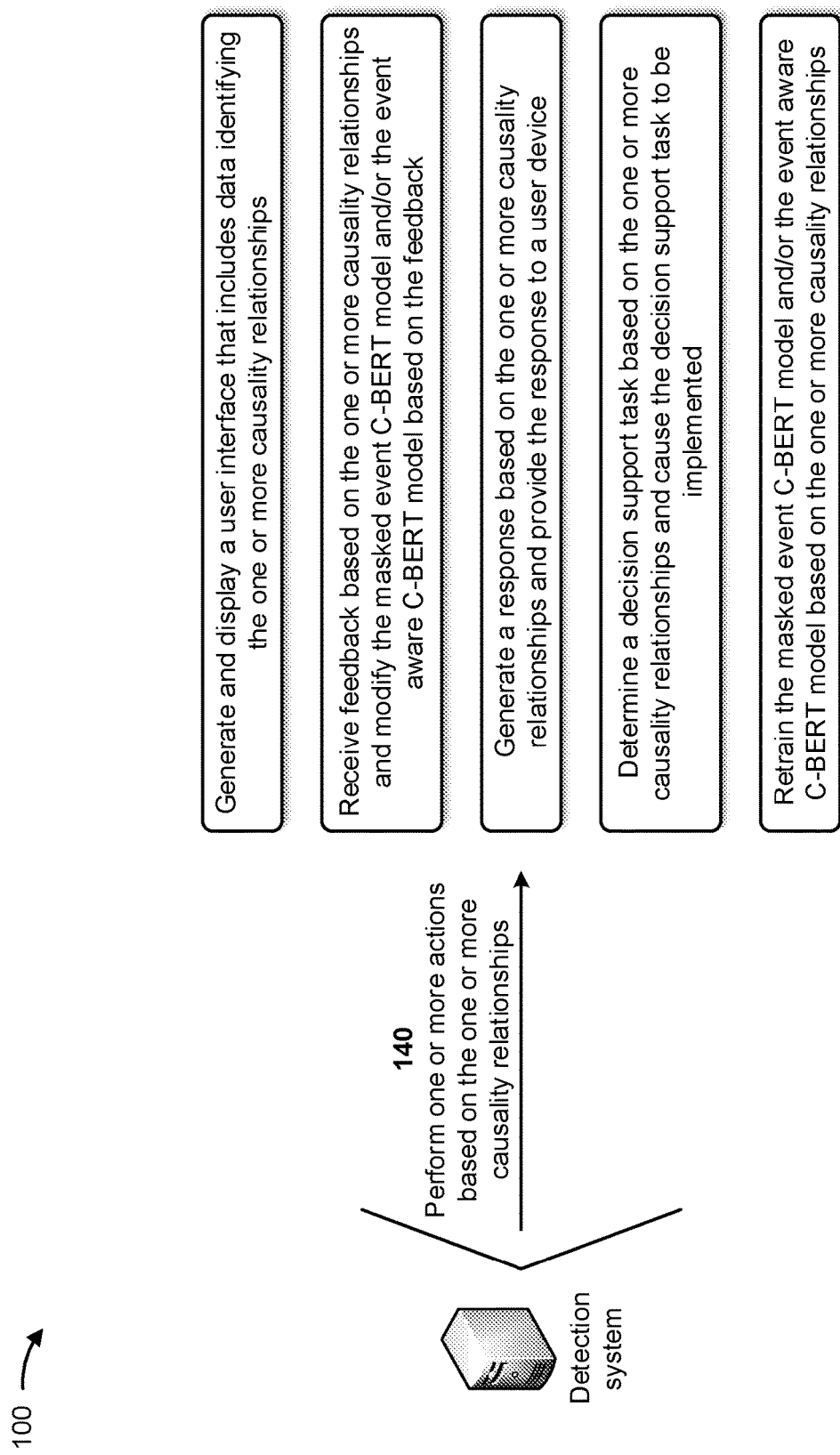

As shown in FIG. 1F, and by reference number 140, the detection system may perform one or more actions based on the one or more causality relationships. In some implementations, the one or more actions include the detection system generating and displaying a user interface that includes data identifying the one or more causality relationships. For example, the detection system may provide the user interface, for display, to the user device so that a user of the user device may review the one or more causality relationships. In this way, the user may utilize the one or more causality relationships for question answering, to determine an adverse drug effect, to determine a drug-drug interaction, for a decision support system, and/or the like. This conserves human resources, computing resources, networking resources, and/or the like that would otherwise have been wasted by utilizing incomplete machine learning models that generate incorrect causality relationships.

In some implementations, the one or more actions include the detection system receiving feedback based on the one or more causality relationships and modifying the masked event C-BERT model and/or the event aware C-BERT model based on the feedback. For example, the detection system may receive the feedback based on the one or more causality relationships from the user of the user device (e.g., indicating whether the causality relationships are correct). The detection system may modify the masked event C-BERT model and/or the event aware C-BERT model, based on the feedback, to improve the masked event C-BERT model and/or the event aware C-BERT model. Thus, the detection system may conserve computing resources associated with identifying, obtaining, and/or generating historical data for training the masked event C-BERT model and/or the event aware C-BERT model, relative to other systems for identifying, obtaining, and/or generating historical data for training machine learning models.

In some implementations, the one or more actions include the detection system generating a response based on the one or more causality relationships and providing the response to the user device. For example, if the one or more causality relationships relate to a question posed by a user of the user device, the detection system may generate a response to the question based on the one or more causality relationships and may provide the response to the user device. In this way, the user may utilize the one or more causality relationships for question answering, which conserves human resources, computing resources, networking resources, and/or the like that would otherwise have been wasted by utilizing incomplete machine learning models that generate incorrect causality relationships.

In some implementations, the one or more actions include the detection system determining a decision support task based on the one or more causality relationships and causing the decision support task to be implemented. For example, if the one or more causality relationships relate to determining a solution to the problem, the detection system may determine the solution based on the causality relationships and may provide the solution to the user device. In this way, the user may utilize the one or more causality relationships for decision support tasks, which conserves human resources, computing resources, networking resources, and/or the like that would otherwise have been wasted by utilizing incomplete machine learning models that generate incorrect causality relationships.

In some implementations, the one or more actions include the detection system retraining the masked event C-BERT model and/or the event aware C-BERT model based on the one or more causality relationships. The detection system may utilize the one or more causality relationships as additional training data for retraining the masked event C-BERT model and/or the event aware C-BERT model, thereby increasing the quantity of training data available for training the masked event C-BERT model and/or the event aware C-BERT model. Accordingly, the detection system may conserve computing resources associated with identifying, obtaining, and/or generating historical data for training the masked event C-BERT model and/or the event aware C-BERT model relative to other systems for identifying, obtaining, and/or generating historical data for training machine learning models.

In this way, the detection system utilizes machine learning models and in-domain and out-of-domain data distribution to predict a causality relationship between events expressed in natural language text. The detection system may provide an understanding of causality between events expressed in the natural language text. The events may be a nominal, a phrase, or a span of text in an event statement. The detection system may utilize language models and variants of language models that combine event information, sentence argument structure, and overall sentence context to determine the causality understanding between events. For example, the language models may determine a cause-effect interaction between events expressed in a text expression. Pre-training the language models with out-of-domain data distribution improves performance of the language models, and indicates that the language models may learn implicit structural representation in natural language text. This, in turn, conserves human resources, computing resources, networking resources, and/or the like that would otherwise have been wasted by manually training supervised machine learning models, generating machine learning models that are incomplete, generating machine learning models that do not scale, and/or the like.

As indicated above, FIGS. 1A-1F are provided as an example. Other examples may differ from what is described with regard to FIGS. 1A-1F. The number and arrangement of devices shown in FIGS. 1A-1F are provided as an example. In practice, there may be additional devices, fewer devices, different devices, or differently arranged devices than those shown in FIGS. 1A-1F. Furthermore, two or more devices shown in FIGS. 1A-1F may be implemented within a single device, or a single device shown in FIGS. 1A-1F may be implemented as multiple, distributed devices. Additionally, or alternatively, a set of devices (e.g., one or more devices) shown in FIGS. 1A-1F may perform one or more functions described as being performed by another set of devices shown in FIGS. 1A-1F.

Figure 2:
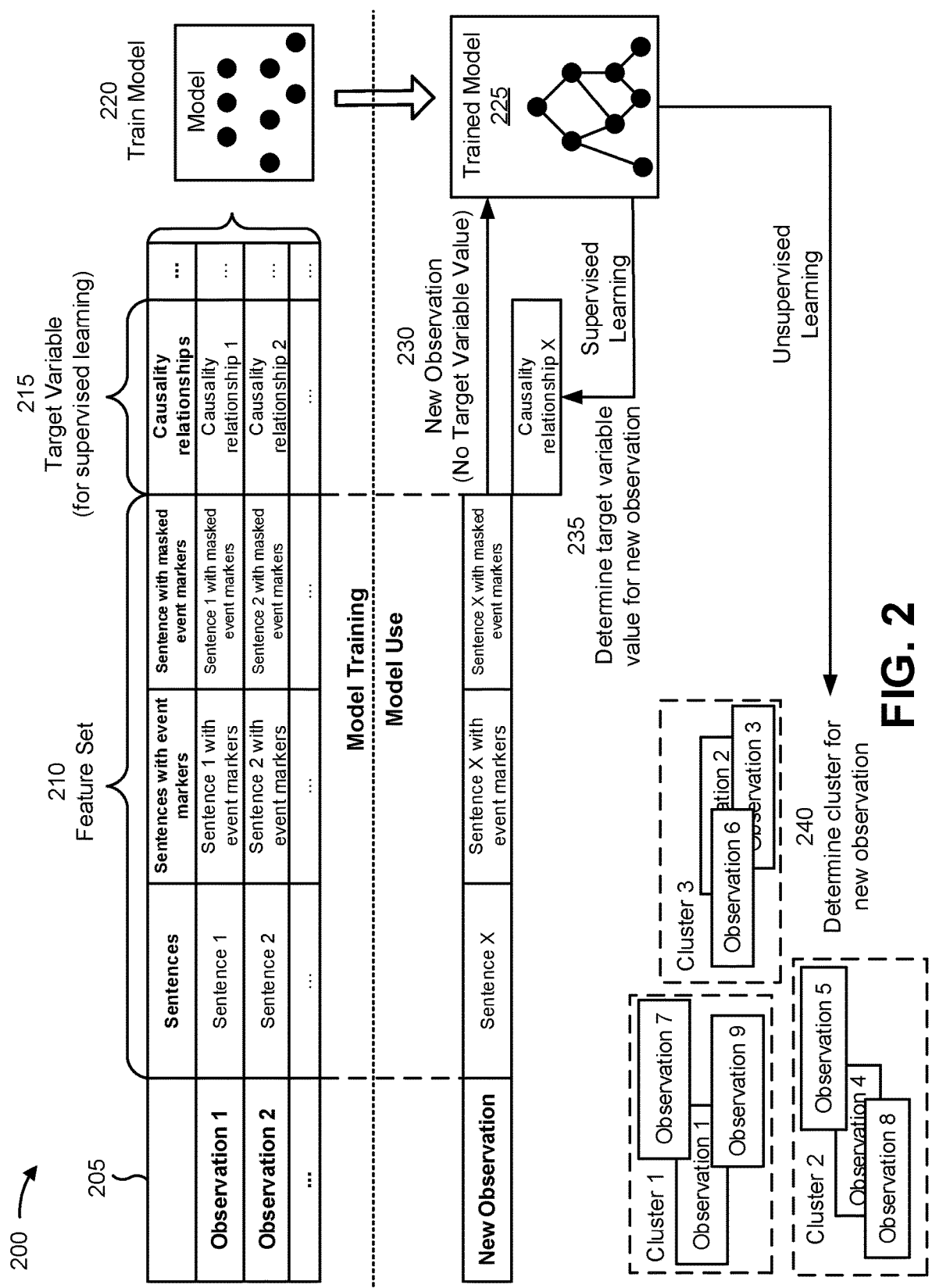
FIG. 2 is a diagram illustrating an example of training and using a machine learning model in connection with predicting a causality relationship between events expressed in natural language text.

FIG. 2 is a diagram illustrating an example 200 of training and using a machine learning model (e.g., the masked event C-BERT model or the event aware C-BERT model) in connection with predicting a causality relationship between events expressed in natural language text. The machine learning model training and usage described herein may be performed using a machine learning system. The machine learning system may include or may be included in a computing device, a server, a cloud computing environment, and/or the like, such as the detection system described in more detail elsewhere herein.

As shown by reference number 205, a machine learning model may be trained using a set of observations. The set of observations may be obtained from historical data, such as data gathered during one or more processes described herein. In some implementations, the machine learning system may receive the set of observations (e.g., as input) from the detection system, as described elsewhere herein.

As shown by reference number 210, the set of observations includes a feature set. The feature set may include a set of variables, and a variable may be referred to as a feature. A specific observation may include a set of variable values (or feature values) corresponding to the set of variables. In some implementations, the machine learning system may determine variables for a set of observations and/or variable values for a specific observation based on input received from the detection system. For example, the machine learning system may identify a feature set (e.g., one or more features and/or feature values) by extracting the feature set from structured data, by performing natural language processing to extract the feature set from unstructured data, by receiving input from an operator, and/or the like.

As an example, a feature set for a set of observations may include a first feature of sentences, a second feature of sentences with event markers, a third feature of sentences with masked event markers, and so on. As shown, for a first observation, the first feature may have a value of creator of sentence 1, the second feature may have a value of sentence 1 with event markers, the third feature may have a value of sentence data 1 with marked event markers, and so on. These features and feature values are provided as examples and may differ in other examples.

As shown by reference number 215, the set of observations may be associated with a target variable. The target variable may represent a variable having a numeric value, may represent a variable having a numeric value that falls within a range of values or has some discrete possible values, may represent a variable that is selectable from one of multiple options (e.g., one of multiple classes, classifications, labels, and/or the like), may represent a variable having a Boolean value, and/or the like. A target variable may be associated with a target variable value, and a target variable value may be specific to an observation. In example 200, the target variable is causality relationships, which has a value of causality relationship 1 for the first observation.

The target variable may represent a value that a machine learning model is being trained to predict, and the feature set may represent the variables that are input to a trained machine learning model to predict a value for the target variable. The set of observations may include target variable values so that the machine learning model can be trained to recognize patterns in the feature set that lead to a target variable value. A machine learning model that is trained to predict a target variable value may be referred to as a supervised learning model.

In some implementations, the machine learning model may be trained on a set of observations that do not include a target variable. This may be referred to as an unsupervised learning model. In this case, the machine learning model may learn patterns from the set of observations without labeling or supervision, and may provide output that indicates such patterns, such as by using clustering and/or association to identify related groups of items within the set of observations.

As shown by reference number 220, the machine learning system may train a machine learning model using the set of observations and using one or more machine learning algorithms, such as a regression algorithm, a decision tree algorithm, a neural network algorithm, a k-nearest neighbor algorithm, a support vector machine algorithm, and/or the like. After training, the machine learning system may store the machine learning model as a trained machine learning model 225 to be used to analyze new observations.

As shown by reference number 230, the machine learning system may apply the trained machine learning model 225 to a new observation, such as by receiving a new observation and inputting the new observation to the trained machine learning model 225. As shown, the new observation may include a first feature of sentence X, a second feature of sentence X with event markers, a third feature of sentence X with masked event markers, and so on, as an example. The machine learning system may apply the trained machine learning model 225 to the new observation to generate an output (e.g., a result). The type of output may depend on the type of machine learning model and/or the type of machine learning task being performed. For example, the output may include a predicted value of a target variable, such as when supervised learning is employed. Additionally, or alternatively, the output may include information that identifies a cluster to which the new observation belongs, information that indicates a degree of similarity between the new observation and one or more other observations, and/or the like, such as when unsupervised learning is employed.

As an example, the trained machine learning model 225 may predict a value of causality relationship X for the target variable of causality relationships, as shown by reference number 235. Based on this prediction, the machine learning system may provide a first recommendation, may provide output for determination of a first recommendation, may perform a first automated action, may cause a first automated action to be performed (e.g., by instructing another device to perform the automated action), and/or the like.

In some implementations, the trained machine learning model 225 may classify (e.g., cluster) the new observation in a cluster, as shown by reference number 240. The observations within a cluster may have a threshold degree of similarity. As an example, if the machine learning system classifies the new observation in a first cluster (e.g., a sentence cluster), then the machine learning system may provide a first recommendation. Additionally, or alternatively, the machine learning system may perform a first automated action and/or may cause a first automated action to be performed (e.g., by instructing another device to perform the automated action) based on classifying the new observation in the first cluster.

As another example, if the machine learning system were to classify the new observation in a second cluster (e.g., a sentence with event markers cluster), then the machine learning system may provide a second (e.g., different) recommendation and/or may perform or cause performance of a second (e.g., different) automated action.

In some implementations, the recommendation and/or the automated action associated with the new observation may be based on a target variable value having a particular label (e.g., classification, categorization, and/or the like), may be based on whether a target variable value satisfies one or more thresholds (e.g., whether the target variable value is greater than a threshold, is less than a threshold, is equal to a threshold, falls within a range of threshold values, and/or the like), may be based on a cluster in which the new observation is classified, and/or the like.

In this way, the machine learning system may apply a rigorous and automated process to predict a causality relationship between events expressed in natural language text. The machine learning system enables recognition and/or identification of tens, hundreds, thousands, or millions of features and/or feature values for tens, hundreds, thousands, or millions of observations, thereby increasing accuracy and consistency and reducing delay associated with predicting a causality relationship between events expressed in natural language text relative to requiring computing resources to be allocated for tens, hundreds, or thousands of operators to manually predict a causality relationship between events expressed in natural language text.

As indicated above, FIG. 2 is provided as an example. Other examples may differ from what is described in connection with FIG. 2.

Figure 3:
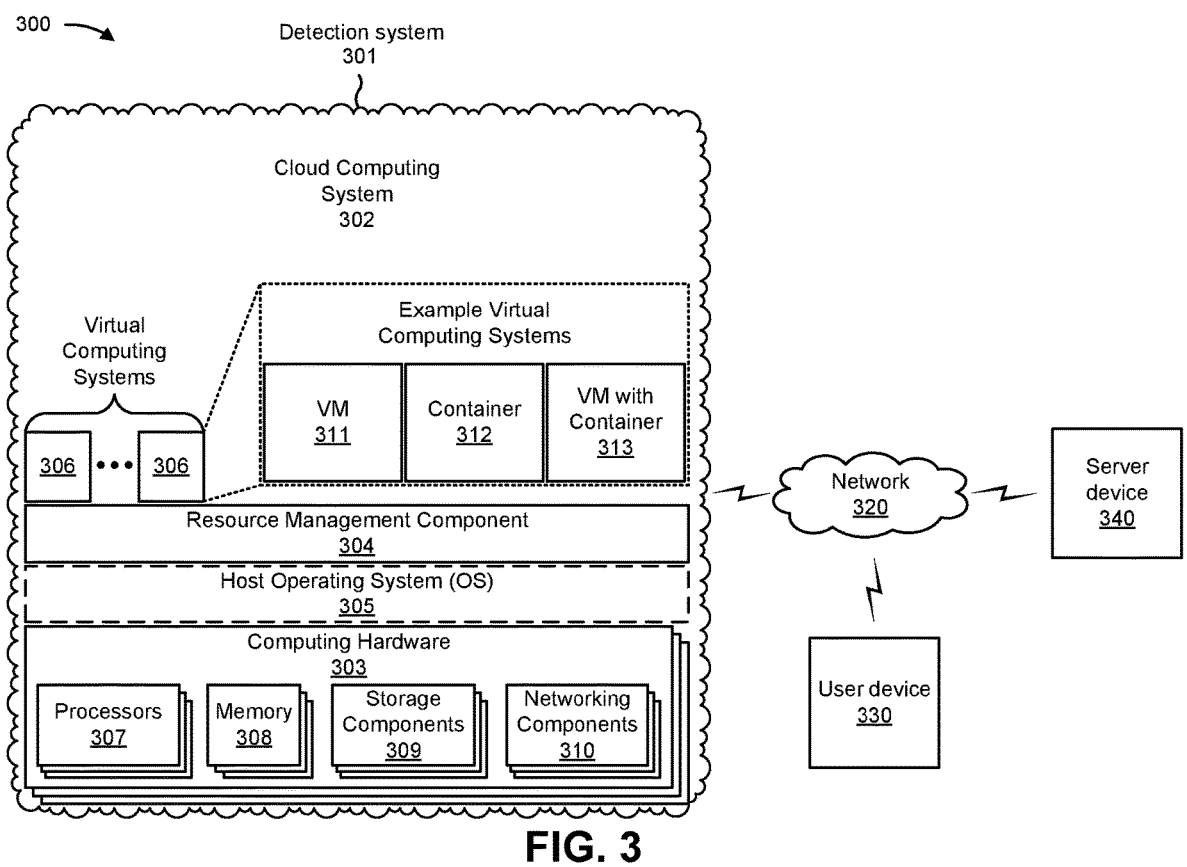
FIG. 3 is a diagram of an example environment in which systems and/or methods described herein may be implemented.

FIG. 3 is a diagram of an example environment 300 in which systems and/or methods described herein may be implemented. As shown in FIG. 3, environment 300 may include a detection system 301, which may include one or more elements of and/or may execute within a cloud computing system 302. The cloud computing system 302 may include one or more elements 303-313, as described in more detail below. As further shown in FIG. 3, environment 300 may include a network 320, a user device 330, and/or a server device 340. Devices and/or elements of environment 300 may interconnect via wired connections and/or wireless connections.

The cloud computing system 302 includes computing hardware 303, a resource management component 304, a host operating system (OS) 305, and/or one or more virtual computing systems 306. The resource management component 304 may perform virtualization (e.g., abstraction) of computing hardware 303 to create the one or more virtual computing systems 306. Using virtualization, the resource management component 304 enables a single computing device (e.g., a computer, a server, and/or the like) to operate like multiple computing devices, such as by creating multiple isolated virtual computing systems 306 from computing hardware 303 of the single computing device. In this way, computing hardware 303 can operate more efficiently, with lower power consumption, higher reliability, higher availability, higher utilization, greater flexibility, and lower cost than using separate computing devices.

Computing hardware 303 includes hardware and corresponding resources from one or more computing devices. For example, computing hardware 303 may include hardware from a single computing device (e.g., a single server) or from multiple computing devices (e.g., multiple servers), such as multiple computing devices in one or more data centers. As shown, computing hardware 303 may include one or more processors 307, one or more memories 308, one or more storage components 309, and/or one or more networking components 310. Examples of a processor, a memory, a storage component, and a networking component (e.g., a communication component) are described elsewhere herein.

The resource management component 304 includes a virtualization application (e.g., executing on hardware, such as computing hardware 303) capable of virtualizing computing hardware 303 to start, stop, and/or manage one or more virtual computing systems 306. For example, the resource management component 304 may include a hypervisor (e.g., a bare-metal or Type 1 hypervisor, a hosted or Type 2 hypervisor, and/or the like) or a virtual machine monitor, such as when the virtual computing systems 306 are virtual machines 311. Additionally, or alternatively, the resource management component 304 may include a container manager, such as when the virtual computing systems 306 are containers 312. In some implementations, the resource management component 304 executes within and/or in coordination with a host operating system 305.

A virtual computing system 306 includes a virtual environment that enables cloud-based execution of operations and/or processes described herein using computing hardware 303. As shown, a virtual computing system 306 may include a virtual machine 311, a container 312, a hybrid environment 313 that includes a virtual machine and a container, and/or the like. A virtual computing system 306 may execute one or more applications using a file system that includes binary files, software libraries, and/or other resources required to execute applications on a guest operating system (e.g., within the virtual computing system 306) or the host operating system 305.

Although the detection system 301 may include one or more elements 303-313 of the cloud computing system 302, may execute within the cloud computing system 302, and/or may be hosted within the cloud computing system 302, in some implementations, the detection system 301 may not be cloud-based (e.g., may be implemented outside of a cloud computing system) or may be partially cloud-based. For example, the detection system 301 may include one or more devices that are not part of the cloud computing system 302, such as device 400 of FIG. 4, which may include a stand-alone server or another type of computing device. The detection system 301 may perform one or more operations and/or processes described in more detail elsewhere herein.

Network 320 includes one or more wired and/or wireless networks. For example, network 320 may include a cellular network, a public land mobile network (PLMN), a local area network (LAN), a wide area network (WAN), a private network, the Internet, and/or the like, and/or a combination of these or other types of networks. The network 320 enables communication among the devices of environment 300.

User device 330 includes one or more devices capable of receiving, generating, storing, processing, and/or providing information, as described elsewhere herein. User device 330 may include a communication device and/or a computing device. For example, user device 330 may include a wireless communication device, a user equipment (UE), a mobile phone (e.g., a smart phone or a cell phone, among other examples), a laptop computer, a tablet computer, a handheld computer, a desktop computer, a gaming device, a wearable communication device (e.g., a smart wristwatch or a pair of smart eyeglasses, among other examples), an Internet of Things (IoT) device, or a similar type of device. User device 330 may communicate with one or more other devices of environment 300, as described elsewhere herein.

Server device 340 includes one or more devices capable of receiving, generating, storing, processing, providing, and/or routing information, as described elsewhere herein. Server device 340 may include a communication device and/or a computing device. For example, server device 340 may include a server, an application server, a client server, a web server, a database server, a host server, a proxy server, a virtual server (e.g., executing on computing hardware), a server in a cloud computing system, a device that includes computing hardware used in a cloud computing environment, or a similar type of device. Server device 340 may communicate with one or more other devices of environment 300, as described elsewhere herein.

The number and arrangement of devices and networks shown in FIG. 3 are provided as an example. In practice, there may be additional devices and/or networks, fewer devices and/or networks, different devices and/or networks, or differently arranged devices and/or networks than those shown in FIG. 3. Furthermore, two or more devices shown in FIG. 3 may be implemented within a single device, or a single device shown in FIG. 3 may be implemented as multiple, distributed devices. Additionally, or alternatively, a set of devices (e.g., one or more devices) of environment 300 may perform one or more functions described as being performed by another set of devices of environment 300.

FIG. 4 is a diagram of example components of a device 400, which may correspond to detection system 301, user device 330, and/or server device 340. In some implementations, detection system 301, user device 330, and/or server device 340 may include one or more devices 400 and/or one or more components of device 400. As shown in FIG. 4, device 400 may include a bus 410, a processor 420, a memory 430, a storage component 440, an input component 450, an output component 460, and a communication component 470.

Bus 410 includes a component that enables wired and/or wireless communication among the components of device 400. Processor 420 includes a central processing unit, a graphics processing unit, a microprocessor, a controller, a microcontroller, a digital signal processor, a field-programmable gate array, an application-specific integrated circuit, and/or another type of processing component. Processor 420 is implemented in hardware, firmware, or a combination of hardware and software. In some implementations, processor 420 includes one or more processors capable of being programmed to perform a function. Memory 430 includes a random access memory, a read only memory, and/or another type of memory (e.g., a flash memory, a magnetic memory, and/or an optical memory).

Storage component 440 stores information and/or software related to the operation of device 400. For example, storage component 440 may include a hard disk drive, a magnetic disk drive, an optical disk drive, a solid-state disk drive, a compact disc, a digital versatile disc, and/or another type of non-transitory computer-readable medium. Input component 450 enables device 400 to receive input, such as user input and/or sensed inputs. For example, input component 450 may include a touch screen, a keyboard, a keypad, a mouse, a button, a microphone, a switch, a sensor, a global positioning system component, an accelerometer, a gyroscope, an actuator, and/or the like. Output component 460 enables device 400 to provide output, such as via a display, a speaker, and/or one or more light-emitting diodes. Communication component 470 enables device 400 to communicate with other devices, such as via a wired connection and/or a wireless connection. For example, communication component 470 may include a receiver, a transmitter, a transceiver, a modem, a network interface card, an antenna, and/or the like.

Device 400 may perform one or more processes described herein. For example, a non-transitory computer-readable medium (e.g., memory 430 and/or storage component 440) may store a set of instructions (e.g., one or more instructions, code, software code, program code, and/or the like) for execution by processor 420. Processor 420 may execute the set of instructions to perform one or more processes described herein. In some implementations, execution of the set of instructions, by one or more processors 420, causes the one or more processors 420 and/or the device 400 to perform one or more processes described herein. In some implementations, hardwired circuitry may be used instead of or in combination with the instructions to perform one or more processes described herein. Thus, implementations described herein are not limited to any specific combination of hardware circuitry and software.

The number and arrangement of components shown in FIG. 4 are provided as an example. Device 400 may include additional components, fewer components, different components, or differently arranged components than those shown in FIG. 4. Additionally, or alternatively, a set of components (e.g., one or more components) of device 400 may perform one or more functions described as being performed by another set of components of device 400.

FIG. 5 is a flowchart of an example process 500 for utilizing machine learning models and in-domain and out-of-domain data distribution to predict a causality relationship between events expressed in natural language text. In some implementations, one or more process blocks of FIG. 5 may be performed by a device (e.g., detection system 301). In some implementations, one or more process blocks of FIG. 5 may be performed by another device or a group of devices separate from or including the device, such as a user device (e.g., user device 330) and/or a server device (e.g., server device 340). Additionally, or alternatively, one or more process blocks of FIG. 5 may be performed by one or more components of device 400, such as processor 420, memory 430, storage component 440, input component 450, output component 460, and/or communication component 470.

As shown in FIG. 5, process 500 may include receiving training data that includes one or more datasets associated with natural language processing (block 510). For example, the device may receive training data that includes one or more datasets associated with natural language processing, as described above.

As further shown in FIG. 5, process 500 may include masking the training data to generate masked training data (block 520). For example, the device may mask the training data to generate masked training data, as described above.

As further shown in FIG. 5, process 500 may include training a masked event C-BERT model, with the masked training data, to generate pretrained weights and a trained masked event C-BERT model (block 530). For example, the device may train a masked event C-BERT model, with the masked training data, to generate pretrained weights and a trained masked event C-BERT model, as described above.

As further shown in FIG. 5, process 500 may include training an event aware C-BERT model, with the training data and the pretrained weights, to generate a trained event aware C-BERT model (block 540). For example, the device may train an event aware C-BERT model, with the training data and the pretrained weights, to generate a trained event aware C-BERT model, as described above.

As further shown in FIG. 5, process 500 may include receiving natural language text data identifying one or more natural language events (block 550). For example, the device may receive natural language text data identifying one or more natural language events, as described above.

As further shown in FIG. 5, process 500 may include processing the natural language text data, with the trained masked event C-BERT model, to determine one or more weights (block 560). For example, the device may process the natural language text data, with the trained masked event C-BERT model, to determine one or more weights, as described above.

As further shown in FIG. 5, process 500 may include processing the natural language text data and the one or more weights, with the trained event aware C-BERT model, to predict one or more causality relationships between the one or more natural language events (block 570). For example, the device may process the natural language text data and the one or more weights, with the trained event aware C-BERT model, to predict one or more causality relationships between the one or more natural language events, as described above.

As further shown in FIG. 5, process 500 may include performing one or more actions, based on the one or more causality relationships between the one or more natural language events (block 580). For example, the device may perform one or more actions, based on the one or more causality relationships between the one or more natural language events, as described above.

Process 500 may include additional implementations, such as any single implementation or any combination of implementations described below and/or in connection with one or more other processes described elsewhere herein.

In a first implementation, the one or more datasets include one or more of a Semeval 20078 dataset, a Semeval 2010 dataset, an adverse drug effect dataset, or a drug-drug interaction dataset.

In a second implementation, alone or in combination with the first implementation, the one or more datasets include one or more sentences and one or more pairs of event interactions, and process 500 includes annotating the one or more sentences with event descriptions, and assigning one or more labels for each pair of the one or more pairs of event interactions.

In a third implementation, alone or in combination with one or more of the first and second implementations, masking the training data to generate the masked training data includes replacing event descriptions, provided in the training data, with blank tokens to generate the masked training data.

In a fourth implementation, alone or in combination with one or more of the first through third implementations, each of the masked event C-BERT model and the event aware C-BERT model is a feed-forward neural network model built on a bidirectional encoder representations from transformers model.

In a fifth implementation, alone or in combination with one or more of the first through fourth implementations, training the masked event C-BERT model, with the masked training data, to generate the pretrained weights and the trained masked event C-BERT model includes generating vectors for masked events in the masked training data; averaging the vectors to determine a sentence context and final contexts for the masked events; and processing the sentence context and the final contexts with a non-linear activation layer and a fully connected layer to generate the pretrained weights and the trained masked event C-BERT model.

In a sixth implementation, alone or in combination with one or more of the first through fifth implementations, training the event aware C-BERT model, with the training data and the pretrained weights, to generate the trained event aware C-BERT model includes generating vectors for events in the training data; averaging the vectors, based on the pretrained weights, to determine a sentence context and final contexts for the events; and processing the sentence context and the final contexts with a non-linear activation layer and a fully connected layer to generate the trained event aware C-BERT model.

In a seventh implementation, alone or in combination with one or more of the first through sixth implementations, the one or more natural language events include one or more of a nominal in the natural language text data, a phrase in the natural language text data, or a span of text in the natural language text data.

In an eighth implementation, alone or in combination with one or more of the first through seventh implementations, processing the natural language text data and the one or more weights, with the trained event aware C-BERT model, to predict the one or more causality relationships between the one or more natural language events includes combining event information, sentence argument structure, and overall sentence context, associated with the one or more natural language events, to predict the one or more causality relationships between the one or more natural language events.

In a ninth implementation, alone or in combination with one or more of the first through eighth implementations, each of the one or more causality relationships between the one or more natural language events includes a cause-effect interaction between two or more events expressed in a text expression.

In a tenth implementation, alone or in combination with one or more of the first through eleventh implementations, performing the one or more actions includes one or more of generating and displaying a user interface that includes data identifying the one or more causality relationships, or generating a response based on the one or more causality relationships and providing the response to a user device.

In an eleventh implementation, alone or in combination with one or more of the first through tenth implementations, performing the one or more actions includes one or more of determining a decision support task based on the one or more causality relationships and causing the decision support task to be implemented, or retraining the masked event C-BERT model or the event aware C-BERT model based on the one or more causality relationships.

In a twelfth implementation, alone or in combination with one or more of the first through eleventh implementations, performing the one or more actions includes providing the one or more causality relationships for display, receiving feedback based on providing the one or more causality relationships for display, and modifying the masked event C-BERT model or the event aware C-BERT model based on the feedback.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

The foregoing disclosure provides illustration and description, but is not intended to be exhaustive or to limit the implementations to the precise form disclosed. Modifications may be made in light of the above disclosure or may be acquired from practice of the implementations.

As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

As used herein, satisfying a threshold may, depending on the context, refer to a value being greater than the threshold, greater than or equal to the threshold, less than the threshold, less than or equal to the threshold, equal to the threshold, and/or the like, depending on the context.

Although particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, and/or the like), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:
    receiving, by a device, training data that includes one or more datasets associated with natural language processing;
    masking, by the device, the training data to generate masked training data;
    training, by the device, a masked event cause-effect bidirectional encoder representations from transformers (C-BERT) model, with the masked training data, to generate pretrained weights and a trained masked event C-BERT model;
    training, by the device, an event aware C-BERT model, with the training data and the pretrained weights, to generate a trained event aware C-BERT model,
        wherein training the event aware C-BERT model comprises:
            determining a sentence context and final contexts for events based on one or more events in the training data and the pretrained weights; and
            processing the sentence context and the final contexts for the events with a non-linear activation layer and a fully connected layer to generate the trained event aware C-BERT model;
    receiving, by the device, natural language text data identifying one or more natural language events;

processing, by the device, the natural language text data, with the trained masked event C-BERT model, to determine one or more weights;

processing, by the device, the natural language text data and the one or more weights, with the trained event aware C-BERT model, to predict one or more causality relationships between the one or more natural language events; and performing, by the device, one or more actions, based on the one or more causality relationships between the one or more natural language events.

2. The method of claim 1, wherein the one or more datasets include one or more of:
a Semeval 2007 dataset,
a Semeval 2010 dataset,
an adverse drug effect dataset, or
a drug-drug interaction dataset.

3. The method of claim 1, wherein the one or more datasets include one or more sentences and one or more pairs of event interactions, and the method further comprises:
annotating the one or more sentences with event descriptions; and
assigning one or more labels for each pair of the one or more pairs of event interactions.

4. The method of claim 1, wherein masking the training data to generate the masked training data comprises:
replacing event descriptions, provided in the training data, with blank tokens to generate the masked training data.

5. The method of claim 1, wherein each of the masked event C-BERT model and the event aware C-BERT model is a feed-forward neural network model built on a bidirectional encoder representations from transformers model.

6. The method of claim 1, wherein training the masked event C-BERT model, with the masked training data, to generate the pretrained weights and the trained masked event C-BERT model comprises:
generating vectors for masked events in the masked training data;
averaging the vectors to determine a sentence context and final contexts for the masked events; and
processing the sentence context and the final contexts with the non-linear activation layer and the fully connected layer to generate the pretrained weights and the trained masked event C-BERT model.

7. The method of claim 1, wherein training the event aware C-BERT model, with the training data and the pretrained weights, to generate the trained event aware C-BERT model comprises:
generating vectors for the events in the training data; and
averaging the vectors, based on the pretrained weights, to determine the sentence context and the final contexts for the events.

8. A device, comprising:
one or more memories; and
one or more processors, communicatively coupled to the one or more memories, configured to:
receive training data that includes one or more datasets associated with natural language processing;
replace event descriptions, provided in the training data, with blank tokens to generate masked training data;
train a masked event cause-effect bidirectional encoder representations from transformers (C-BERT) model, with the masked training data, to generate pretrained weights and a trained masked event C-BERT model, wherein the one or more processors to train the masked event C-BERT model, with the masked training data, to generate the pretrained weights and the trained masked event C-BERT model, are to:
determine a sentence context and final contexts for masked events based on one or more masked events in the masked training data; and
process the sentence context and the final contexts for the masked events with a non-linear activation layer and a fully connected layer to generate the pretrained weights and the trained masked event C-BERT model;
train an event aware C-BERT model, with the training data and the pretrained weights, to generate a trained event aware C-BERT model;
receive natural language text data identifying one or more natural language events;
process the natural language text data, with the trained masked event C-BERT model, to determine one or more weights;
process the natural language text data and the one or more weights, with the trained event aware C-BERT model, to predict one or more causality relationships between the one or more natural language events; and
perform one or more actions, based on the one or more causality relationships between the one or more natural language events.

9. The device of claim 8, wherein the one or more natural language events include one or more of:
a nominal in the natural language text data,
a phrase in the natural language text data, or
a span of text in the natural language text data.

10. The device of claim 8, wherein the one or more processors, when processing the natural language text data and the one or more weights, with the trained event aware C-BERT model, to predict the one or more causality relationships between the one or more natural language events, are configured to:
combine event information, sentence argument structure, and overall sentence context, associated with the one or more natural language events, to predict the one or more causality relationships between the one or more natural language events.

11. The device of claim 8, wherein each of the one or more causality relationships between the one or more natural language events includes a cause-effect interaction between two or more events expressed in a text expression.

12. The device of claim 8, wherein the one or more processors, when performing the one or more actions, are configured to one or more of:
generate and display a user interface that includes data identifying the one or more causality relationships; or
generate a response based on the one or more causality relationships and provide the response to a user device.

13. The device of claim 8, wherein the one or more processors, when performing the one or more actions, are configured to one or more of:
determine a decision support task based on the one or more causality relationships and cause the decision support task to be implemented; or
retrain the masked event C-BERT model or the event aware C-BERT model based on the one or more causality relationships.

14. The device of claim 8, wherein the one or more processors, when performing the one or more actions, are configured to:

provide the one or more causality relationships for display;

receive feedback based on providing the one or more causality relationships for display; and modify the masked event C-BERT model or the event aware C-BERT model based on the feedback.

15. A non-transitory computer-readable medium storing a set of instructions, the set of instructions comprising:

one or more instructions that, when executed by one or more processors of a device, cause the device to:

receive data that includes one or more datasets associated with natural language processing;

annotate one or more sentences, provided in the one or more datasets, with event descriptions to generate annotated data;

assign one or more labels for each pair of event interactions, provided in the one or more datasets, to generate labeled data;

combine the annotated data and the labeled data to form training data;

mask the training data to generate masked training data;

train a masked event cause-effect bidirectional encoder representations from transformers (C-BERT) model, with the masked training data, to generate pretrained weights and a trained masked event C-BERT model;

wherein the one or more instructions, that cause the device to train the masked event C-BERT model, with the masked training data, to generate the pretrained weights and the trained masked event C-BERT model, cause the device to:

determine a sentence context and final contexts for masked events based on one or more masked events in the masked training data; and process the sentence context and the final contexts for the masked events with a non-linear activation layer and a fully connected layer to generate the pretrained weights and the trained masked event C-BERT model;

train an event aware C-BERT model, with the training data and the pretrained weights, to generate a trained event aware C-BERT model;

receive natural language text data identifying one or more natural language events;

process the natural language text data, with the trained masked event C-BERT model, to determine one or more weights;

process the natural language text data and the one or more weights, with the trained event aware C-BERT model, to predict one or more causality relationships between the one or more natural language events; and perform one or more actions, based on the one or more causality relationships between the one or more natural language events.

16. The non-transitory computer-readable medium of claim 15, wherein the one or more instructions, that cause the device to mask the training data to generate the masked training data, cause the device to:

replace event descriptions, provided in the training data, with blank tokens to generate the masked training data.

17. The non-transitory computer-readable medium of claim 15, wherein the one or more instructions, that cause the device to train the masked event C-BERT model, with the masked training data, to generate the pretrained weights and the trained masked event C-BERT model, cause the device to:

generate vectors for the masked events in the masked training data; and average the vectors to determine the sentence context and the final contexts for the masked events.

18. The non-transitory computer-readable medium of claim 15, wherein the one or more instructions, that cause the device to train the event aware C-BERT model, with the training data and the pretrained weights, to generate the trained event aware C-BERT model, cause the device to:

generate vectors for events in the training data;

average the vectors, based on the pretrained weights, to determine a sentence context and final contexts for the events; and process the sentence context and the final contexts with the non-linear activation layer and the fully connected layer to generate the trained event aware C-BERT model.

19. The non-transitory computer-readable medium of claim 15, wherein the one or more instructions, that cause the device to perform the one or more actions, cause the device to one or more of:

generate and display a user interface that includes data identifying the one or more causality relationships;

generate a response based on the one or more causality relationships and provide the response to a user device;

determine a decision support task based on the one or more causality relationships and cause the decision support task to be implemented; or retrain the masked event C-BERT model or the event aware C-BERT model based on the one or more causality relationships.

20. The non-transitory computer-readable medium of claim 15, wherein the one or more instructions, that cause the device to perform the one or more actions, cause the device to:

provide the one or more causality relationships for display;

receive feedback based on providing the one or more causality relationships for display; and modify the masked event C-BERT model or the event aware C-BERT model based on the feedback.

* * * * *